(12) United States Patent
Matsumura et al.

(10) Patent No.: US 6,730,629 B2
(45) Date of Patent: May 4, 2004

(54) ASYMMETRIC PHOSPHINE LIGAND

(75) Inventors: Kazuhiko Matsumura, Hiratsuka (JP); Takao Saito, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/315,255

(22) Filed: Dec. 10, 2002

(65) Prior Publication Data

US 2003/0139285 A1 Jul. 24, 2003

(30) Foreign Application Priority Data

Dec. 10, 2001 (JP) .......................... 2001-375256

(51) Int. Cl.$^7$ .............................. B01J 31/24; C07F 9/50
(52) U.S. Cl. .......................... 502/166; 556/21; 568/12; 568/17
(58) Field of Search .............................. 556/13, 20, 21; 568/8, 12, 17; 502/162, 166

(56) References Cited

U.S. PATENT DOCUMENTS

| | | | |
|---|---|---|---|
| 5,008,457 A | 4/1991 | Burk | 568/12 |
| 5,171,892 A | 12/1992 | Burk | 568/12 |
| 6,207,868 B1 | 3/2001 | Zhang | 568/814 |
| 6,278,024 B1 | 8/2001 | Zhang | 568/17 |
| 6,380,416 B2 | 4/2002 | Zhang | 558/156 |
| 6,399,787 B1 | 6/2002 | Zhang | 548/469 |
| 6,624,320 B2 * | 9/2003 | Matsumura et al. | 556/21 |
| 2001/0047113 A1 | 11/2001 | Zhang | 568/14 |

FOREIGN PATENT DOCUMENTS

| | | |
|---|---|---|
| WO | 99/59721 A1 | 11/1999 |
| WO | 00/11008 A1 | 3/2000 |
| WO | 00/26220 A1 | 5/2000 |

OTHER PUBLICATIONS

CA:139:69031 abs of Advanced Synthesis and Catalysis by Matsumura et al 345(1+2) pp 180–184 2003.*

Brunner, Henri, et al.; "Asymmetric Catalyses. XXXIII. New Optically Active Phospholanes Derived from Tartaric Acid"; *Journal of Organometallic Chemistry*; vol. 328, pp. 71–80, 1987.

Holz, Jens, et al.; "Synthesis of a New Class of Functionalized Chiral Bisphospholane Ligands and the Application of Enantioselective Hydrogenations"; *Journal of Organic Chemistry*; vol. 63, No. 22, pp. 8031–8033; 1998.

Kottsieper, Konstantin W. et al.; "Synthesis of enantiopure $C_1$ symmetric diphosphines and phosphino–phosphOnites with ortho–phenylene backbones"; *Tetrahedron: Asymmetry*; vol. 12, pp. 1159–1169; 2001.

* cited by examiner

Primary Examiner—Jean F. Vollano
(74) Attorney, Agent, or Firm—Kubovcik & Kubovcik

(57) ABSTRACT

A phosphine compound having excellent properties (chemical selectivity, enantioselectivity, catalytic activity) as a catalyst for asymmetric syntheses, especially asymmetric hydrogenations. A phosphine-phospholane compound represented by the following formula (1):

a phosphine-primary phosphine intermediate; a transition metal complex including the phosphine-phospholane compound of formula (1) and a transition metal, and a catalyst including the transition metal complex.

8 Claims, No Drawings

ASYMMETRIC PHOSPHINE LIGAND

FIELD OF THE INVENTION

The present invention relates to a novel phosphine-phospholane compound, a production intermediate thereof, a transition metal complex containing the phosphine-phospholane compound as a ligand, a catalyst useful as a catalyst for various asymmetric syntheses, and catalytic asymmetric synthetic technology using the same. Furthermore, the invention relates to a novel optically active phosphine-phospholane compound, a production intermediate thereof, a transition metal complex containing the optically active phosphine-phospholane compound as a ligand, a catalyst useful as a catalyst for various asymmetric syntheses, and catalytic asymmetric synthetic technology using the same.

BACKGROUND OF THE INVENTION

Hitherto, many reports have been made on transition metal complex catalysts capable of being utilized in catalytic asymmetric syntheses such as asymmetric hydrogenations, asymmetric transfer hydrogenation reductions, asymmetric hydrosilylations, asymmetric hydroborations, asymmetric hydroformylations, asymmetric isomerizations of olefins, and asymmetric Heck reactions. Particularly, it is reported that complexes of transition metals such as ruthenium, iridium, rhodium, palladium, and nickel containing various optically active phosphines as ligands exhibit excellent performance as catalysts for asymmetric syntheses, and some of the catalysts are industrially employed (Asymmetric Catalysis in Organic Synthesis, Ed., R Noyori, Wiley & Sons, New York (1994)). Among these ligands, phospholane-type ligands are disclosed and transition metal complexes containing the ligands are reported to be useful as catalysts for catalytic asymmetric syntheses such as asymmetric hydrogenations ((1) H. Burunner, R. Sievi, J. Organometal. Chem., 1987, 328, 71; (2) WO 91/17998 (BPE); (3) WO 93/01199 (DuPHOS); (4) J. Org. Chem., 1998, 63, 8031 (RoPHOS); (5) WO 00/11008; (6) WO 99/59721 (PennPhos) (7) WO 00/26220; and so forth).

However, all the phospholane-type ligands disclosed in (1) to (6) contain two optically active phospholane rings per one molecule, so that their preparation requires a large amount of expensive optically active 1,3- or 1,4-diols. Moreover, in the synthesis of the diphosphine disclosed in (7), it is necessary to introduce an optically active center onto a phosphorus atom, which is difficult to synthesize. Thus, these ligands are not suitable for practical use.

SUMMARY OF THE INVENTION

It is an object of the invention to provide a novel phosphine compound which can be synthesized from a small amount of an optically active compound and has excellent properties (chemical selectivity, enantioselectivity, catalytic activity) as a catalyst for asymmetric syntheses, especially asymmetric hydrogenations.

As a result of intensive studies for solving the above problem, the present inventors have found that a transition metal complex of an optically active phosphine-phospholane having a specific structure is effective for asymmetric hydrogenations.

Moreover, they have found that the transition metal complex exhibits excellent catalytic activity and enantio- or diastereo-selectivity in asymmetric hydrogenations of olefins such as enamides and β-monosubstituted dehydroamino acid derivatives, and accomplished the invention.

Incidentally, a ligand containing one optically active phospholane ring per one molecule has been reported in "Tetrahedron; Asymmetry 2001, 12, 1159", which discloses the compound and process for producing the same but does not describe the preparation of a complex from a transition metal and the compound or asymmetric hydrogenation of a substrate in the presence of the complex, still less a compound having a substituent other than phenyl group on the phosphine and a process for producing the same.

DETAILED DESCRIPTION OF THE INVENTION

The following will explain the invention in detail.

The phosphine-phospholane compound of the invention is represented by the general formula (1):

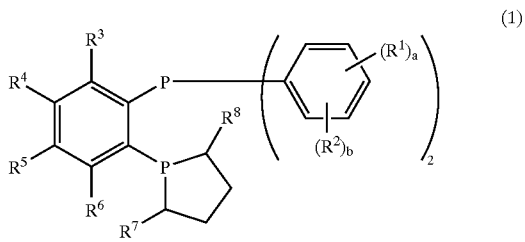

(1)

(wherein $R^1$ represents hydrogen atom, a linear or branched alkyl group having 1 to 4 carbon atoms; $R^2$ represents hydrogen atom or $OR^{21}$, where $R^{21}$ represents an alkyl group having 1 to 4 carbon atoms, a represents an integer of 1 to 2, b represents an integer of 1 to 3, the sum of a and b represents an integer of 2 to 3, provided that at least one of $R^1$ and $R^2$ is not a hydrogen atom; $R^3$, $R^4$, $R^5$ and $R^6$ are the same or different, and each represents hydrogen atom, an alkyl group having 1 to 6 carbon atoms, or an alkoxy group having 1 to 6 carbon atoms, and each of $R^3$ and $R^4$, $R^4$ and $R^5$, and $R^5$ and $R^6$ may be combined together to form a ring which may contain one or more (preferably 1 to 2) oxygen atoms; and $R^7$ and $R^8$ are the same or different, and each represents (1) a linear or branched alkyl group having 1 to 6 carbon atoms, (2) a cycloalkyl group having 3 to 7 carbon atoms, (3) a perfluoroalkyl group, (4) a phenyl group, (5) a phenyl group having one or more (preferably 1 to 5) substituents each selected from the group consisting of an alkyl group having 1 to 6 carbon atoms, an alkyl group having 1 to 6 carbon atoms which is substituted by one or more (preferably 1 to 5) halogen atoms, an alkoxy group having 1 to 6 carbon atoms, and a halogen atom, (6) an aralkyl group having 7 to 12 carbon atoms, or (7) a ring-substituted aralkyl group).

The alkyl group having 1 to 4 carbon atoms for the above $R^1$ is selected from the group consisting of a methyl group, ethyl group, n-propyl group, iso-propyl group, n-butyl group, iso-butyl group, sec-butyl group, and tert-butyl group.

The alkyl group having 1 to 4 carbon atoms for the above $R^{21}$ is selected from the group consisting of a methyl group, ethyl group, n-propyl group, iso-propyl group, n-butyl group, iso-butyl group, sec-butyl group, and tert-butyl group.

The alkyl group having 1 to 6 carbon atoms for $R^3$, $R^4$, $R^5$ or $R^6$ is selected from the group consisting of a methyl group, ethyl group, n-propyl group, iso-propyl group, n-butyl group, iso-butyl group, sec-butyl group, tert-butyl group, n-pentyl group, iso-pentyl group, neo-pentyl group, tert-pentyl group, 2-methylpentyl group, n-hexyl group, and iso-hexyl group, and the alkoxy group having 1 to 6 carbon atoms includes a methoxy group, ethoxy group, n-propyloxy group, iso-propyloxy group, n-butoxy group, iso-butoxy group, sec-butoxy group, tert-butoxy group, n-pentyloxy group, iso-pentyloxy group, neo-pentyloxy group, tert-pentyloxy group, 2-methylpentyloxy group, n-hexyloxy group, and iso-hexyloxy group.

Furthermore, each of (1) $R^3$ and $R^4$, (2) $R^4$ and $R^5$, and (3) $R^5$ and $R^6$ may be together combined to form a ring, where the ring is preferably a ring having 5 to 10 carbon atoms, which is formed together with other carbon atoms. The ring may contain one or more (preferably 1 to 2) oxygen atoms. And the ring may have one or more (preferably 1 to 5) substituents.

Specific examples of a ring containing one or more (preferably 1 to 2) oxygen atoms include methylenedioxy group, ethylenedioxy group, or propylenedioxy group, and of a ring having 5 to 10 carbon atoms includes benzene, indane, tetrahydronaphthalene, indene, dihydronaphthalene, fluorene, naphthalene, anthracene, phenanthrene, and the like. The substituent for the rings includes an alkyl group having 1 to 6 carbon atoms, an alkoxy group having 1 to 6 atoms, an alkyl group having 1 to 6 carbon atoms substituted by one or more (preferably 1 to 5) halogen atoms, a halogen atom, amino group, an amino group substituted by one or more (preferably 1 to 5) alkyl groups, and the like. The alkyl group having 1 to 6 carbon atoms and the alkoxy group having 1 to 6 atoms are selected from those described above.

The linear or branched alkyl group having 1 to 6 carbon atoms for the above $R^7$ or $R^8$ is selected from the same groups as described above. The cycloalkyl group having 3 to 7 carbon atoms is preferably a cyclopropyl group, methylcyclopropyl group, cyclobutyl group, cyclopentyl group, 2-methylcyclopentyl group, 3-methylcyclopentyl group, cyclohexyl group, 2-methylcyclohexyl group, 3-methylcyclohexyl group, 4-methylcyclohexyl group, or cycloheptyl group.

The phenyl group may have one or more (preferably 1 to 5) substituents. The alkyl group having 1 to 6 carbon atoms as the substituent is selected from the same groups as described above. The alkyl group by which the phenyl group is substituted may be further substituted by one or more (preferably 1 to 5) halogen atoms each selected from fluorine atom, chlorine atom, iodine atom, or the like. Moreover, the halogen atom by which the phenyl group is substituted is selected from fluorine atom, chlorine atom, iodine atom, or the like, and the alkoxy group having 1 to 6 atoms is selected from the same groups as described above.

The perfluoroalkyl group includes trifluoromethyl group and pentafluoroethyl group.

The aralkyl group having 7 to 12 carbon atoms is preferably a benzyl group, 2-phenylethyl group, 1-phenylpropyl group, 2-phenylpropyl group, 3-phenylpropyl group, 1-phenylbutyl group, 2-phenylbutyl group, 3-phenylbutyl group, 4-phenylbutyl group, 1-phenylpentyl group, 2-phenylpentyl group, 3-phenylpentyl group, 4-phenylpentyl group, 5-phenylpentyl group, 1-phenylhexyl group, 2-phenylhexyl group, 3-phenylhexyl group, 4-phenylhexyl group, 5-phenylhexyl group, or 6-phenylhexyl group. Moreover, the substituent on the aralkyl group includes an alkyl group having 1 to 6 carbon atoms, an alkoxy group having 1 to 6 carbon atoms, and a halogen atom, each of which is selected from those the same as above.

The phosphine-phospholane compound represented by the general formula (1) is preferably a compound represented by the general formula (10) or a compound represented by the general formula (11):

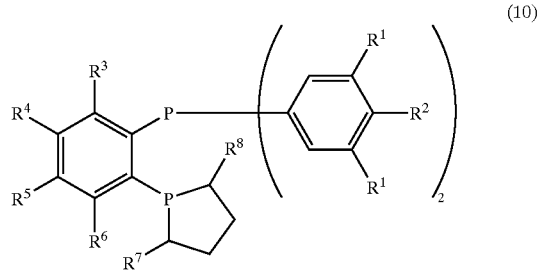

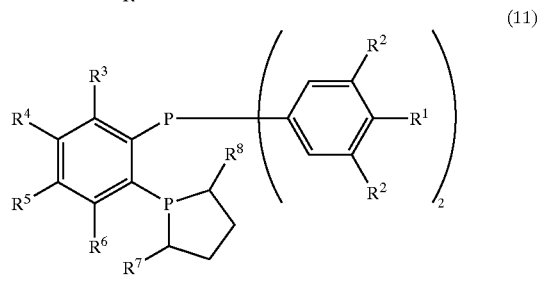

(wherein $R^1$ to $R^8$ are the same as above).

The phosphine-primary phosphine intermediate of the invention is represented by the general formula (2):

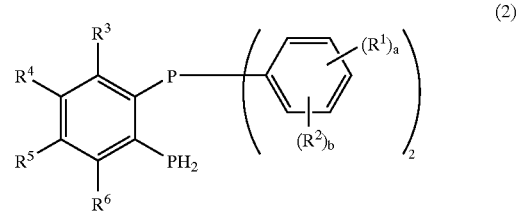

(wherein $R^1$ to $R^6$, a, and b are the same as above).

The phosphine-primary phosphine compound represented by the general formula (2) is preferably a compound represented by the general formula (12) or a compound represented by the general formula (13):

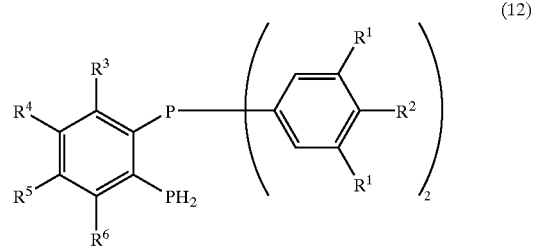

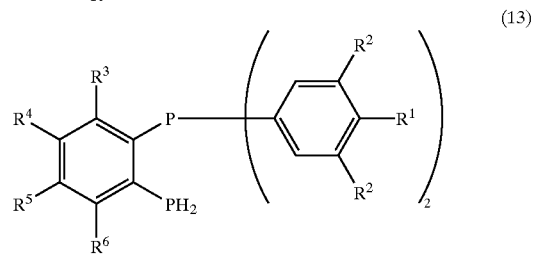

(wherein $R^1$ to $R^6$ are the same as above),

The compound represented by the general formula (2) is a production intermediate of the compound represented by the general formula (1).

The invention includes racemic compounds, meso-isomers, and optically active compounds of the above compounds.

The following will explain the production method of these compounds.

First, in order to avoid complication, the representative production method of the compounds of the invention is specifically explained using the following compound: 1-Bis(3,5-di-t-butyl-4-methoxyphenyl)phosphino-2-((2S,5S)-2,5-di methylphospholano)benzene (hereinafter sometimes referred to as (S,S)-Me-UCAP-DTBM) among the compounds included in the invention as an example. Of course, the invention is not limited to the examples.

(S,S)-Me-UCAP-DTBM can be represented by the following formula (3).

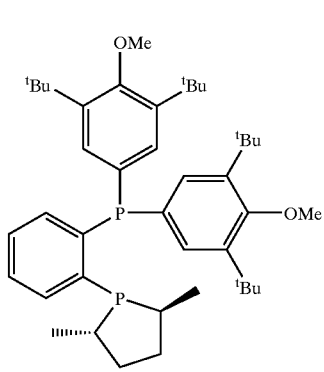

(3)

(wherein Me represent methyl group; $^t$Bu represent tert-butyl group.)

For example, referring to the reaction sequence shown below, 2-bromophenol (4) is reacted with trifluoromethanesulfonic anhydride to form 2-(trifluoromethanesulfonyl)oxy-bromobenzene (5), which is then reacted with bis(3,5-di-t-butyl-4-methoxyphenyl)phosphine oxide in the presence of a palladium complex catalyst to obtain bis(3,5-di-t-butyl-4-methoxyphenyl)(2-bromophenyl)phosphine oxide (6). Next, the compound (6) is reduced with trichlorosilane in the presence of N,N'-dimethylaniline to obtain bis(3,5-di-t-butyl-4-methoxyphenyl)(2-bromophenyl)phosphine (7). The compound (7) is reacted with diethyl chlorophosphonite in the presence of n-butyllithium to obtain diethyl 2-[bis(3,5-di-t-butyl-4-methoxyphenyl)phosphino]phenylphosphonite (8). Then, the compound (8) is reduced with lithium aluminum hydride in the presence of trimethylsilyl chloride to form 2-[bis(3,5-di-t-butyl-4-methoxyphenyl)phosphino]phenylphosphine (9). Thereafter, in the presence of n-butyllithium, the compound (9) is reacted with dimesylate of (2R,5R)-2,5-hexanediol, which is producible, for example, according to the method described in the literature (Tetrahedron: Asymmetry, 1991, 2, 569), whereby the aimed (S,S)-Me-UCAP-DTBM (3) can be produced in a high efficiency.

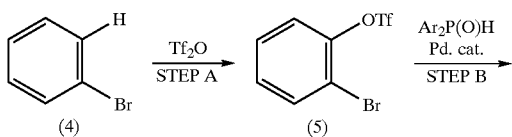

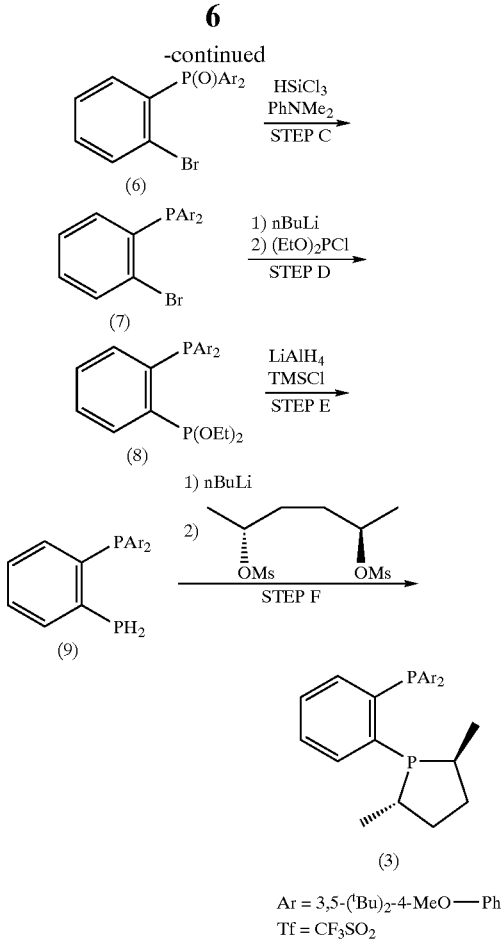

Ar = 3,5-($^t$Bu)$_2$-4-MeO—Ph
Tf = CF$_3$SO$_2$

The reaction in Step A is a reaction wherein the hydroxyl group of a 2-hydroxyaryl halide (4) is triflated to form a 2-(trifluoromethanesulfonyloxy)-aryl halide (5) and is carried out in accordance with the method of triflation of 1,1'-binaphthol described in known literature (Tetrahedron Lett., 1990, 31, 6321). If necessary, the compound (5) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction in Step B is a reaction wherein a 2-(halophenyl)phosphine oxide (6) is formed by reacting 2-(trifluoromethanesulfonyl)oxy-aryl halide (5) with a phosphine oxide compound in the presence of a catalyst of a transition metal such as palladium, the reaction being carried out in accordance with the method described in known literature (Tetrahedron Lett., 1990, 31, 6321). If necessary, the compound (6) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of Step C is a reaction wherein the resulting 2-(halophenyl)phosphine oxide (6) is reduced to form 2-(halophenyl)phosphine (7). The reduction to obtain the phosphine is achieved by treating the phosphine oxide with a reagent which is known as a reducing agent in the field of organic synthesis, for example, a silane compound such as trichlorosilane, diphenylsilane or hexachlorodisilane. The amount of the reducing agent to be used ranges from 1 to 10 equivalents, preferably 2 to 8 equivalents, relative to the phosphine oxide.

The reaction is preferably carried out in the presence of a solvent and use can be made of a usual solvent which does not adversely influence the reaction. Preferred is an inert solvent including an ether such as diethyl ether, diisopropyl ether, tetrahydrofuran (THF), 1,4-dioxane, or 1,2-dimethoxyethane, or a hydrocarbon such as pentane, hexane, or methylcyclohexane, or an aromatic hydrocarbon such as benzene, toluene, xylene, chlorobenzene, or a halogenated hydrocarbon such as chloroform, dichloromethane, 1,2-dichloroethane, or carbon tetrachloride. These solvents maybe used solely or as a mixed solvent. The reaction can be suitably carried out in the presence of an amine such as trimethylamine, triethyamine, N,N-dimethyaniline, N,N-diethylaniline or pyridine. Moreover, the reaction can be suitably carried out under an inert gas atmosphere such as argon or nitrogen. The reaction temperature is from about −50° C. to about a reflux temperature of the solvent, and usually, the reaction is preferably carried out at a temperature of from room temperature to about a reflux temperature of the solvent. If necessary, the compound (7) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of the first step of Step D is a reaction wherein the C—Br bond of the compound (7) is cleaved and metalated. The reagent for use in the metalation includes an alkali metal (e.g., lithium, sodium, or potassium), an alkaline earth metal (e.g., magnesium), or a derivative thereof (e.g., sodium-cyclopentadiene, sodium bistrimethylsilylamide, potassium hydride, potassium amide, or a Grignard reagent). Preferably, the C-Br bond can be cleaved and metalated by treating the compound with a reagent which is known as a lithiation reagent in the field of organic synthesis, such as methyllithium, n-butyllithium, sec-butyllithium, tert-butyllithium, phenyllithium, or lithium diiso-propylamide.

The reaction is preferably carried out in the presence of a solvent and use can be made of a usual solvent which does not adversely influence the reaction. Preferred is an inert solvent including an ether such as diethyl ether, diisopropyl ether, tetrahydrofuran (THF), 1,4-dioxane, or 1,2-dimethoxyethane, or a hydrocarbon such as pentane, hexane, or methylcyclohexane. These solvents may be used solely or as a mixed solvent. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −100° C. to about room temperature, and usually, the reaction is preferably carried out under a cooled condition, for example, under cooling with a dry ice-acetone bath or dry ice-2-propanol bath.

Next, the reaction of the second step of Step D is a reaction wherein a phosphine derivative is formed by the reaction with a phosphorus-containing compound such as chlorophosphonite. The phosphorus-containing compound includes dimethyl chlorophosphonite, diethyl chlorophosphonite, di(n-propyl) chlorophosphonite, diisopropyl chlorophosphonite, di(n-butyl) chlorophosphonite, and diphenyl chlorophosphonite. Preferably, a phosphine-phosphonite can be obtained by treatment with an easily available dialkyl chlorophosphonite, e.g., dimethyl chlorophosphonite or diethyl chlorophosphonite.

The reaction is preferably carried out in the presence of a solvent, and use can be made of a usual solvent which does not adversely influence the reaction. The solvents illustrated in the first step of Step D can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The temperature at the dropwise addition of a chlorophosphite is from about −100° C. to about a reflux temperature of the solvent, and the addition is usually carried out under a cooled condition, for example, under cooling with a dry ice-acetone bath or dry ice-2-propanol bath. The reaction temperature after the dropwise addition is from −100° C. to about reflux temperature of the solvent used, and usually, the reaction is preferably carried out at room temperature. If necessary, the compound (8) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of Step E is a reaction wherein the resulting phosphine-phosphonite is reduced to form a tertiary phosphine-primary phosphine. The reduction is achieved by treating the phosphine-phosphonite with a reagent which is known as a reducing agent in the field of organic synthesis, for example, a metal hydride such as lithium aluminum hydride. The amount of the reducing agent to be used ranges from 1 to 10 equivalents, preferably 2 to 8 equivalents relative to the phosphine-phosphonite.

The reaction is preferably carried out in the presence of a solvent, and use can be made of a usual solvent which does not adversely influence the reaction. Preferred is an inert solvent including an ether such as diethyl ether, diisopropyl ether, tetrahydrofuran (THF), 1,4-dioxane, or 1,2-dimethoxyethane, a hydrocarbon such as pentane, hexane, or methylcyclohexane, an aromatic hydrocarbon such as benzene, toluene, or chlorobenzene, or a halogenated hydrocarbon such as chloroform, dichloromethane, 1,2-dichloroethane, or carbon tetrachloride. These solvents maybe used solely or as a mixed solvent. Moreover, the reaction can be suitably carried out in the presence of a Lewis acid such as trimethylsilyl chloride. Furthermore, the reaction can be suitably carried out under an inert gas atmosphere such as argon or nitrogen. The reaction temperature is from about −50° C. to about a reflux temperature of the solvent, and usually, the reaction is preferably carried out at a temperature of −30° C. to room temperature. If necessary, the compound (9) thus obtained can be isolated and purified by a known separation-purification procedure, for example, concentration, concentration under reduced pressure, solvent extraction, crystallization, recrystallization, or chromatography, but it may be used in the next step as a reaction mixture without isolation.

The reaction of the first step of final Step F is a reaction of dimetalation of the resulting tertiary phosphine-primary phosphine by cleaving its P—H bond. The reagent for use in the metalation includes an alkali metal (e.g., lithium, sodium, or potassium), an alkaline earth metal (e.g., magnesium), or a derivative thereof (sodium-cyclopentadiene, sodium bistrimethylsilylamide, potassium hydride, potassium amide, or a Grignard reagent). Preferably, the dimetalation can be achieved by treating the compound with a reagent which is known as a lithiation reagent in the field of organic synthesis, such as methyllithium, n-butyllithium, sec-butyllithium, tert-butyllithium, phenyllithium, or lithium diiso-propylamide to cleave the P—H bond.

The reaction is preferably carried out in the presence of a solvent, and use can be made of a usual solvent which does not adversely influence the reaction. The solvents illustrated in the first step of Step D can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −30° C. to about room temperature, and usually, the reaction is preferably carried out at a temperature of 0° C. to room temperature.

The reaction of the second step of final Step F is a reaction wherein the resulting bis (metal) compound is reacted with a bis (alkyl sulfonate) derivative of an optically active 1,4-diol to form an optically active phosphine-phospholane which is the final product, the diol being producible by using the method described in the literature (Tetrahedron: Asymmetry 1991, 2, 569) and the derivative being obtainable by reacting the diol with an alkylsulfonyl chloride, preferably methanesulfonyl chloride, in the presence of a tertiary amine such as triethylamine.

The reaction is preferably carried out in the presence of a solvent, and use can be made of a usual solvent which does not adversely influence the reaction. The solvents illustrated in the first step of Step D can be used as preferred solvents. If necessary, the reaction can be carried out in the presence of a base such as N,N,N',N'-tetramethylethylenediamine (TMEDA). Moreover, the reaction can be suitably carried out under an inert gas atmosphere such as argon or nitrogen. The reaction temperature is from about −30° C. to about a reflux temperature of the solvent, and usually, the reaction is preferably carried out at a temperature of 0° C. to room temperature. If necessary, the resulting optically active phosphine-phospholane compound (3) thus obtained can be isolated and purified by a known separation-purification procedure, for example, concentration, concentration under reduced pressure, solvent extraction, crystallization, recrystallization, or chromatography.

Various compounds of the formula (1) or (2) can be obtained using various 2-bromophenol derivatives instead of the above 2-bromophenol in Step A of the above production method, various diaryl-phosphine oxides (e.g., di(4-tolyl) phosphine oxide, di(4-t-butylphenyl)phosphine oxide, di(4-methoxyphenyl)phosphine oxide, bis(3,5-dimethylphenyl) phosphine oxide, bis(3,5-di-t-butylphenyl)phosphine oxide, bis(3,5-dimethoxyphenyl)phosphine oxide, bis(3,5-dimethyl-4-methoxyphenyl)phosphine oxide) instead of the above bis(3,5-di-t-butyl-4-methoxyphenyl)phosphine oxide in Step B of the production method, and dimesylates of various optically active diols (e.g., 3,6-octanediol, 4,7-decanediol, 3,6-dihydroxy-2,7-dimethyloctane, 1,4-dicyclohexyl-1,4-butanediol, and 1,4-di(trifluoromethyl)-1, 4-butanediol) instead of the above dimesylate of optically active hexanediol in Step F of the production method.

Among the compounds of the invention, the compound (1) particularly an optically active compound (1) is useful as a ligand of a transition metal complex. Furthermore, the compound (2) is useful as a production intermediate of the compound (1).

The following will explain the transition metal complex.
Preferred complexes include the following compounds:
A complex represented by the general formula (3):

$$M_mL_nX_pY_q \tag{3}$$

(wherein M is a transition metal selected from the group consisting of Ir, Rh, Ru, Pd, and Ni and L represents a phosphine-phospholane compound of the present invention represented by the general formula (1); and when M is Ir or Rh, X is Cl, Br, or I, and m=n=p=2 and q=0, when M is Ru, (i) X is Cl, Br, or I, Y represents a trialkylamino group, and m=n=2, p=4 and q=1, (ii) X is Cl, Br, or I, Y represents pyridyl group or a ring-substituted pyridyl group, and m=n=1, p=2, and q=2, (iii) X is a carboxylate group, and m=n=1, p=2 and q=0, or (iv) X is Cl, Br, or I, and m=n=p=2 and q=0, when M is Pd, (i) X is Cl, Br, or I, and m=n=1, p=2, and q=0 or (ii) X is an allyl group, and m=n=p=2 and q=0, and when M is Ni, X is Cl, Br, or I, and m=n=1, p=2, and q=0).
A complex represented by the general formula (4):

$$[M_mL_nX_pY_q]Z_s \tag{4}$$

(wherein M is a transition metal selected from the group consisting of Ir, Rh, Ru, Pd, and Ni and L represents the phosphine-phospholane compound of the present invention represented by the general formula (1); and when M is Ir or Rh, (i) X is 1,5-cyclooctadiene or norbornadiene, Z is $BF_4$, $ClO_4$, OTf, $PF_6$, $SbF_6$, or $BPh_4$, and m=n=p=s 1 and q=0 or (ii) Z is $BF_4$, $ClO_4$, OTf, $PF_6$, $SbF_6$, or $BPh_4$, and m=s 1, n=2 and q=0, when M is Ru, (i) X is Cl, Br, or I, Y represents an aromatic compound or olefin compound which is a neutral ligand, Z is Cl, Br, I, 13, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2 or (iii) X is Cl, Br, or I, Z is $Me_2NH_2$ or $Et_2NH_2$, and m=n=2, p=5, q=0, s=1, and when M is Pd or Ni, Z is $BF_4$, $ClO_4$, OTf, $PF_6$, $SbF_6$, or $BPh_4$, and m=n=1, p=q=0, and s=2, wherein Ph represents a phenyl group, Me represents a methyl group, Et represents a ethyl group and Tf represents a triflate group ($SO_2CF_3$))

A transition metal which forms the complex includes rhodium, ruthenium, iridium, palladium, nickel, and the like.

These transition metal complexes can be produced by a known method. By the way, with regard to the symbols used in the formulae shown in the following transition metal complexes, L represents an optically active compound among the compounds (1) of the invention, cod represents 1,5-cyclooctadiene, nbd represents norbornadiene, Tf represents a triflate group ($SO_2CF_3$), Ph represents phenyl group, Ac represents acetyl group, and Et represents ethyl group.

Rhodium Complex:

As a specific example of producing a rhodium complex, the complex can be synthesized by reacting bis(cycloocta-1,5-diene) rhodium (I) tetrafluoroborate salt with, for example, (S,S)-Me-UCAP-DTBM of the invention according to the method described in "4th edition Jikken Kagaku Koza (Lecture of Experimental Chemistry)", vol. 18, Organic Metal Complexes, 1991, Maruzen, pp. 339–344, edited by the Chemical Society of Japan. The following can be mentioned as specific examples of the rhodium complexes.

[Rh(L)Cl]$_2$, [Rh(L)Br]$_2$, [Rh(L)I]$_2$,
[Rh(cod)(L)]BF$_4$, [Rh(cod)(L)]ClO$_4$,
[Rh(cod)(L)]PF$_6$, [Rh(cod)(L)]BPh$_4$, [Rh(cod)(L)]OTf,
[Rh(nbd)(L)]BF$_4$, [Rh(nbd)(L)]ClO$_4$,

[Rh(nbd)(L)]PF$_6$, [Rh(nbd)(L)]BPh$_4$, [Rh(nbd)(L)]OTf, [Rh(L)$_2$]BF$_4$, [Rh(L)$_2$]ClO$_4$, [Rh(L)$_2$]PF$_6$, [Rh(L)$_2$]BPh$_4$, [Rh(L)$_2$]OTf Ruthenium Complex:

As the method for producing a ruthenium complex, the complex can be prepared by heating [Ru(cod)Cl$_2$]$_n$ and Me-UCAP-DTBM at reflux in a toluene solvent in the presence of triethylamine as described in the literature (T. Ikariya, Y. Ishii, H. Kawano, T. Arai, M. Saburi, S. Yoshikawa, and S. Akutagawa, J. Chem. Soc., Chem. Commun., 1988, 922). Moreover, it can also be prepared by heating [Ru (p-cymene) I$_2$]$_2$ and Me-UCAP-DTBM with stirring in dichloromethane and ethanol according to a method described in the literature (K. Mashima, K. Kusano, T. Ohta, R. Noyori, H. Takaya, J. Chem. Soc., Chem. Commun., 1989, 1208). The following can be mentioned as specific examples of the ruthenium complexes.

Ru(OAc)$_2$(L), Ru$_2$Cl$_4$(L)$_2$NEt$_3$,
[RuCl(benzene)(L)]Cl, [RuBr(benzene)(L)]Br, [RuI(benzene)(L)]I,
[RuCl(p-cymene)(L)]Cl, [RuBr(p-cymene)(L)]Br, [RuI(p-cymene)(L)]I,
[Ru(L)](BF$_4$)$_2$, [Ru(L)](ClO$_4$)$_2$, [Ru(L)](PF$_6$)$_2$, [Ru(L)](BPh$_4$)$_2$, [Ru(L)](OTf)$_2$
[{RuCl(L)}$_2$($\mu$-Cl)$_3$][Me$_2$NH$_2$], [{RuBr(L)}$_2$($\mu$-Br)$_3$][Me$_2$NH$_2$], [{RuI(L)}$_2$($\mu$-I)$_3$][Me$_2$NH$_2$]
[{RuCl(L)}$_2$($\mu$-Cl)$_3$]$_3$[Et$_2$NH$_2$], [{RuBr(L)}$_2$($\mu$-Br)][Et$_2$NH$_2$], [{(RuI(L)}$_2$($\mu$-I)$_3$][Et$_2$NH$_2$]

Iridium Complex:

The iridium complex can be prepared by reacting Me-UCAP-DTBM with [Ir (cod) (CH$_3$CN)$_2$]BF$_4$ in tetrahydrofuran according to the method described in the literature (K. Mashima, T. Akutagawa, X. Zhang, T. Taketomi, H. Kumobayashi, S. Akutagawa, J. Organomet. Chem., 1992, 428, 213). The following can be mentioned as specific examples of the iridium complexes.

[Ir(L)Cl]$_2$, [Ir(L)Br]$_2$, [Ir(L)I]$_2$,
[(Ir(cod)(L)]BF$_4$, [Ir(cod)(L)]ClO$_4$,
[Ir(cod)(L)]PF$_6$, [Ir(cod)(L)]BPh$_4$, [Ir(cod)(L)]OTf,
[Ir(nbd)(L)]BF$_4$, [Ir(nbd)(L)]ClO$_4$,
[Ir(nbd)(L)]PF$_6$, [Ir(nbd)(L)]BPh$_4$, [Ir(nbd)(L)]OTf, [Ir(L)$_2$]BF$_4$, [Ir(L)$_2$]ClO$_4$, [Ir(L)$_2$]PF$_6$, [Ir(L)$_2$]BPh$_4$, [Ir(L)$_2$]OTf Palladium Complex:

The palladium complex can be prepared by reacting Me-UCAP-DTBM with π-allylpalladium chloride according to the method described in the literature (Y. Uozumi and T. Hayashi, J. Am. Chem. Soc., 1991, 113, 9887). The following can be mentioned as specific examples of the palladium complexes.

PdCl$_2$(L), (π-allyl)Pd(L), [Pd(L)]BF$_4$, [Pd(L)]ClO$_4$, [Pd(L)]PF$_6$, [Pd(L)]BPh$_4$, [Pd(L)]OTf Nickel Complex:

The nickel complex can be prepared by the method described in "4th edition Jikken Kagaku Koza (Lecture of Experimental Chemistry)", vol. 18, Organic Metal Complexes, 1991, Maruzene, p. 376, edited by the Chemical Society of Japan, or by dissolving Me-UCAP-DTBM and nickel chloride in a mixed solvent of 2-propanol and methanol and heating them with stirring according to the method described in the literature (Y. Uozumi and T. Hayashi, J. Am. Chem. Soc., 113, 9887 (1991)). The following can be mentioned as specific examples of the nickel complexes.

NiCl$_2$(L), NiBr$_2$(L), NiI2(L)

The transition metal complex containing the novel optically active phosphine-phospholane compound as a ligand is useful as a catalyst for asymmetric hydrogenations. In the case of using the complex as the catalyst, the complex may be used after increasing its purity or the complex may be used without purification.

Among the above transition metal complexes, complexes containing rhodium and the optically active phosphine-phospholane compound, 1-bis(3,5-di-t-butyl-4-methoxyphenyl)phosphino-2-((2S,5S)-2,5-di methylphospholano)benzene (hereinafter, sometimes referred to as (S,S)-Me-UCAP-DTBM) as a ligand can achieve a higher enantioselectivity and a higher catalytic activity as compared with rhodium complexes containing BINAP, Me-DuPHOS, or the like as a ligand in the asymmetric hydrogenation of N-benzoyl-1-phenylpropenamine.

The novel diphosphine compound of the invention is particularly useful as a ligand for a transition metal complex. Moreover, the transition metal complex is useful as a catalyst for asymmetric hydrogenations, and also is industrially extremely useful.

The following will explain the invention in detail with reference to Examples and Use Examples, but the invention is by no means limited thereto.

By the way, the instruments employed for measuring physical properties in each Example are as follows. Nuclear magnetic resonance DRX500 (BRUKER JAPAN CO. LTD.)

| | |
|---|---|
| $^1$H NMR | 500.13 MHz |
| $^{31}$P NMR | 202.46 MHz |
| Melting point | Yanaco MP-500D |
| Optical rotation | Nihon Bunko, DIP-4 |
| Gas chromatography | GLC Hewlett Packard 5890-II |
| High performance liquid chromatography | HPLC Shimadzu Corp. LC10AT & SPD10A |
| Mass spectrometry | MASS Hitachi Ltd. M-80B |

EXAMPLE 1

Synthesis of 1-bis(3,5-di-t-butyl-4-methoxyphenyl)phosphino-2-((2S,5S)-2,5-di methylphospholano)benzene (hereinafter, referred to as (S,S)-Me-UCAP-DTBM)

(a) Synthesis of 2-(trifluoromethanesulfonyl)oxybromobenzene (5)

Into a four-neck flask was weighed 250.00 g (1.445 mol) of 2-bromophenol, and the atmosphere of the reaction vessel which was fitted with a thermometer, a condenser tube, and a dropping funnel with a pressure-equalizing tube was completely replaced with nitrogen. Thereto were added 1,500 mL of anhydrous dichloromethane and 171.40 g (2.168 mol) of pyridine, followed by cooling to 0° C. After the dropwise addition of 448.45 g (1.590 mol) of trifluoromethanesulfonic anhydride over a period of 2 hours, the whole was stirred at room temperature for 2 hours. The resulting mixed solution was poured into 500 mL of 2N hydrochloric acid aqueous solution, the mixture was stirred at room temperature for 30 minutes, and then the layers were separated from each other. The resulting organic layer was washed with water and brine and dried over anhydrous magnesium, and then the solvent was removed by evaporation under reduced pressure. The residue was purified by distillation under reduced pressure to obtain the title compound (425.32 g, a colorless oil). Yield 96.5%.

bp: 112–113° C./1995–2128 Pa $^1$H NMR (CDCl$_3$): δ; 7.2–7.4 (m, 3H), 7.6–7.8 (m, 1H)

(b) Synthesis of bis(3,5-di-t-butyl-4-methoxyphenyl)(2-bromophenyl)phosphine Oxide (6)

Into a four-neck flask were weighed 28.71 g (59.0 mmol) of bis(3,5-di-t-butyl-4-methoxyphenyl)phosphine oxide, 1.27 g (2.5 mmol) of Pd$_2$(dba)$_3$CHCl$_3$ (dba represents dibenzylideneacetone), and 1.01 g (2.5 mmol) of 1,3-diphenylphosphinopropane. The atmosphere of the reaction vessel which was fitted with a thermometer, a condenser tube, and a dropping funnel with a pressure-equalizing tube was completely replaced with nitrogen. Thereto were added 150 mL of toluene, 15.00 g (49.2 mmol) of the 2-(trifluoromethanesulfonyl)oxy-bromobenzene (5), and 9.53 g (73.8 mmol) of N,N-diisopropylethylamine, followed by 16 hours of heating at reflux. After the completion of the reaction, the reaction mixture was cooled to room temperature and poured into 150 mL of 5% hydrochloric acid aqueous solution. After 30 minutes of stirring, the layers were separated from each other. The organic layer was washed with water and brine and dried over anhydrous magnesium sulfate. Toluene was removed by evaporation and the residue was purified by silica gel column chromatography to obtain the title compound (30.83 g, a white viscous solid). Yield 97.7%.

$^1$H NMR (CDCl$_3$): δ; 1.35 (s, 36H), 3.69 (s, 6H), 7.35–7.45 (m, 2H) 7.51 (d, J=13.2 Hz 4H), 7.65 (ddd, J=1.2, 3.9, 7.7 Hz, 1H), 7.73 (ddd, J=1.9, 7.7, 12.5 Hz, 1H)

$^{31}$P NMR (CDCl$_3$) δ; 33.3 (s)

EI-MS (m/z): 642 ([M$^+$])

(c) Synthesis of is bis(3,5-di-t-butyl-4-methoxyphenyl)(2-bromophenyl)phosphine (7)

Into a four-neck flask were weighed 28.81 g (44.9 mmol) of the bis(3,5-di-t-butyl-4-methoxyphenyl)(2-bromophenyl)phosphine oxide (6). The atmosphere of the reaction vessel which was fitted with a thermometer, a condenser tube, and a dropping funnel with a pressure-equalizing tube was completely replaced with nitrogen. Thereto were added 300 mL of toluene, 29.92 g (247.0 mmol) of N,N'-dimethylaniline, and 30.41 g (224.5 mmol) of trichlorosilane, followed by 15 hours of heating at reflux. After the completion of the reaction, the reaction mixture was poured into 180 mL of 25% sodium hydroxide aqueous solution at 0° C. to 10° C. After 30 minutes of stirring at room temperature, the layers were separated from each other. The water layer was extracted with toluene (100 mL). The combined organic layer was washed with 1N hydrochloric acid aqueous solution, water and brine and dried over anhydrous magnesium sulfate. Toluene was removed by evaporation and the residue was recrystallized from toluene-methanol to obtain the title compound (24.30 g, a white solid).

Yield 86.5%.

mp: 142–143° C.

$^1$H NMR (CDCl$_3$): δ; 1.31 (s, 36H), 3.68 (s, 6H), 6.71–6.74 (m, 1H) 7.07 (d, J=7.6 Hz, 4H), 7.15–7.23 (m, 2H), 7.57–7.60 (m, 1H)

$^{31}$P NMR (CDCl$_3$): δ; –3.1 (s)

EI-MS (m/z) 626 ([M$^+$])

(d) Synthesis of Diethyl 2-[bis(3,5-di-t-butyl-4-methoxyphenyl)phosphino]phenylphosphonite (8)

Into a four-neck flask was weighed 15.00 g (24.0 mmol) of the bis(3,5-di-t-butyl-4-methoxyphenyl)(2-bromophenyl)phosphine (7). The atmosphere of the reaction vessel which was fitted with a thermometer, a condenser tube, and a dropping funnel with a pressure-equalizing tube was completely replaced with nitrogen, and 150 mL of anhydrous tetrahydrofuran (hereinafter referred to as THF) was added thereto. Thereto was added dropwise 16.2 mL (25.2 mmol) of n-butyllithium-hexane (1.6 M) solution at –78° C. over a period of 30 minutes, followed by 1 hour of stirring at the same temperature. The resulting mixed solution was cooled to –78° C. and thereto was added dropwise a 10 mL THF solution of 4.15 g (25.2 mmol) of diethyl chlorophosphonite (manufactured by Aldrich) over a period of 30 minutes. After the dropwise addition, a cooling bath was removed and the whole was further stirred at room temperature for 15 hours. After the completion of the reaction, THF was removed by evaporation, the residue was dissolved in 50 mL of diethyl ether, and insoluble matter was removed by filtration. The solvent was removed by evaporation and the residue was purified by active alumina column chromatography (eluent: hexane/ethyl acetate 4/1) to obtain the title compound (14.03 g, a pale yellow solid) Yield 91.5%.

mp: 104–105° C.

$^1$H NMR (CD$_2$Cl$_2$): δ; 1.00 (t, J=7.0 Hz, 3H), 1.29 (s, 36H), 3.51–3.57 (m, 2H), 3.65 (s, 6H), 3.78–3.82 (m, 2H), 7.03 (d, J=7.7 Hz, 4H), 7.30–7.34 (m, 2H), 7.39–7.40 (m, 1H), 7.86–7.89 (m, 1H)

$^{31}$P NMR (CD$_2$Cl$_2$): δ; 150.1 (d, J$_{p-p}$=149 Hz), –17.5 (d, J$_{p-p}$=149 Hz)

EI-MS (m/Z): 666 ([M$^+$])

(e) Synthesis of 2-[bis(3,5-di-t-butyl-4-methoxyphenyl)phosphino]phenylphosphine (9)

Under a nitrogen atmosphere, 4.89 g (45.0 mmol) of trimethylsilyl chloride was added dropwise to a 75 mL THF suspension of 1.719 (45.0 mmol) of lithium aluminum hydride at –30° C. over a period of 30 minutes, and after the dropwise addition, the whole was stirred at room temperature for 1.5 hours. Then, a 50 mL THF solution of 10.0 g (15.0 mmol) of the diethyl 2-[bis(3,5-di-t-butyl-4-methoxyphenyl)phosphino]phenylphosphonite (8) was added dropwise at –30° C. over a period of 30 minutes and the whole was stirred at room temperature for 16 hours. Thereto was gradually added dropwise a 15 mL THF solution of 7.5 mL of water at 0° C. to 10° C., and then 30 mL of 1N sodium hydroxide aqueous solution was added. Under a nitrogen atmosphere, the organic layer was decanted and the solvent was removed by evaporation. The residue was dissolved in 30 mL of diethyl ether, and the solution was washed three times with 10 mL of water degassed beforehand and then dried over anhydrous sodium sulfate. The drying agent was removed and the solvent was removed by evaporation to obtain the title compound (8.20 g, a white viscous solid). Yield 94.0%.

mp: 107–108° C.

$^1$H NMR (CD$_2$Cl$_2$): δ; 1.31 (s, 36H), 3.67 (s, 6H),3.95 (dd, J=12.3, 205.3 Hz, 2H), 6.86–6.89 (m, 1H), 7.07 (d, J=8.2 Hz, 4H), 7.21–7.22 (m, 2H), 7.53–7.57 (m, 1H)

$^{31}$P NMR (CD$_2$Cl$_2$): δ; –9.6 (d, J$_{p-p}$=92 Hz), –124.3 (d, J$_{p-p}$=92 Hz)

EI-MS (m/Z): 578 ([M$^+$])

(f) Synthesis of 1-bis(3,5-di-t-butyl-4-methoxyphenyl)phosphino-2-((2S,5S)-2,5-di methylphospholano)benzene (hereinafter, referred to as (S,S)-Me-UCAP-DTBM)

Under a nitrogen atmosphere, 5.00 g (8.6 mmol) of the 2-[bis(3,5-di-t-butyl-4-methoxyphenyl)phosphino]phenylphosphine (9) was dissolved into 100 mL of THF, and 10.7 mL (17.2 mmol) of n-butyllithium-hexane (1.6 M) solution was added dropwise at 0° C. over a period of 30 minutes, followed by 1 hour of stirring at the same temperature. Then, a 5 mL THF solution of 2.36 g (8.6 mmol) of (2R,5R)-2,5-hexanediol bis(methanesulfonate) obtainable by the method described in the literature (M. J. Burk, J. E. Feaster and R. L. Harlow, Tetrahedron: Asymmetry, 1991, 2, 569) and the like was added dropwise thereto at 0° C. over a period of 30 minutes. After the dropwise addition, the whole was stirred at 0° C. for 1 hour and then at room temperature for 16 hours. Thereafter, 1 mL of methanol was added at room temperature and the solvent was removed by evaporation. The resulting residue was purified by active alumina column chromatography (eluent: hexane/dichloromethane=2/1) to obtain the title compound (2.41 g, a white solid). Yield 42.2%.

mp: 65–66° C.

$[\alpha]_D^{29}$ +118.7° (c=1.00, $CH_2Cl_2$)

$^1$H NMR ($CD_2Cl_2$): δ; 0.73 (dd, J=7.2, 9.3 Hz, 3H), 1.05 (dd, J=7.1, 13.7 Hz, 3H), 1.29 (s, 18H), 1.30 (s, 18H), 1.49–1.61 (m, 2H), 2.00–2.06 (m, 1H), 2.15–2.35 (m, 2H), 2.48–2.58 (m, 1H), 3.65 (s, 3H), 3.65 (s, 3H), 6.92–6.95 (m, 1H), 7.05 (d, J=7.1 Hz, 2H), 7.09 (d, J=7.1 Hz, 2H), 7.21–7.24 (m, 1H), 7.28–7.31 (m, 1H), 7.50–7.52 (m, 1H)

$^{31}$P NMR ($CD_2Cl_2$): δ; −1.8 (d, $J_{p-p}$=160 Hz), −13.5 (d, $J_{p-p}$=160 Hz)

EI-MS (m/Z): 660 ([M]$^+$)

EXAMPLE 2

Synthesis of 1-bis(3,5-dimethylphenyl)phosphino-2-((2S,5S)-2,5-dimethylphospholano)benzene (hereinafter, referred to as (S,S)-Me-UCAP-DM)

The title compound (colorless oil) was obtained in a similar manner to Example 1(a) to (f) using bis (3,5-dimethylphenyl)phosphine oxide instead of bis(3,5-di-t-butyl-4-methoxyphenyl)phosphine oxide described in Example 1(b). The yield was 18% starting from 2-bromophenol.

$[\alpha]_D^{29}$ +110.60 (c=1.20, $CH_2Cl_2$)

$^1$H NMR ($CD_2Cl_2$): δ; 0.77 (dd, J=7.1, 9.3 Hz, 3H), 1.04 (dd, J=7.1, 18.7 Hz, 3H), 1.18–1.30 (m, 1H), 1.43–1.53 (m, 1H), 1.92–1.98 (m, 1H), 2.15 (s, 6H), 2.16 (s, 6H), 2.08–2.29 (m, 2H), 2.48–2.54 (m, 1H), 6.74 (d, J=7.7 Hz, 1H), 6.77–6.91 (m, 5H), 7.12 (t, J=7.5 Hz, 1H), 7.20–7.50 (m, 2H), 7.42–7.44 (m, 1H)

$^{31}$P NMR ($CD_2Cl_2$): δ; 0.8 (d, $J_{p-p}$=156 Hz), −10.4 (d, $J_{p-p}$=156 Hz)

EI-MS (m/Z): 432 ([M]$^+$)

EXAMPLE 3

Synthesis of [Rh(cod)((S,S)-Me-UCAP-DTBM)]OTf

Under a nitrogen atmosphere, 67.5 mg (0.147 mmol) of [Rh(cod)$_2$]OTf was dissolved into 5 mL of dichloromethane in a 20 mL Schlenk tube, and then a 5 mL dichloromethane solution of 100.0 mg (0.151 mmol) of (S,S)-Me-UCAP-DTBM was added thereto at room temperature. After 1 hour of stirring at the same temperature, the solvent was removed by evaporation. The residue was washed by hexane to obtain the title compound (140 mg, golden yellow crystals). Yield 95.2%.

$^{31}$P NMR ($CD_2Cl_2$): δ; 74.8 (dd, J=27, 148 Hz), 61.4 (dd, J=27, 148 Hz)

EXAMPLE 4

Synthesis of [Rh(cod)((S,S)-Me-UCAP-DM)]OTf

Under a nitrogen atmosphere, 108.0 mg (0.231 mmol) of [Rh(cod)$_2$]OTf was dissolved into 5 mL of dichloromethane in a 20 mL Schlenk tube, and then a 5 mL dichloromethane solution of 104.7 mg (0.242 mmol) of (S,S)-Me-UCAP-DTBM was added thereto at room temperature. After 1 hour of stirring at the same temperature, the solvent was removed by evaporation. The residue was washed by hexane to obtain the title compound (150 mg, orange crystals). Yield 82.0%.

$^{31}$P NMR ($CD_2Cl_2$): δ; 74.5 (dd, J=26.2, 147.7 Hz), 60.7 (dd, J=27.5, 149.4 Hz)

EXAMPLES 5 AND 6, AND COMPARATIVE EXAMPLES 1 And 2

Asymmetric Hydrogenation of N-benzoyl-1-phenylpropenamine

Under a nitrogen atmosphere, 0.0018 mmol of [Rh(cod)(L)]OTf, 213.6 mg (0.9 mmol) of N-benzoyl-1-phenylpropenamine, and 3 mL of methanol were placed in a stainless autoclave, followed by 15 hours of stirring at 30° C. under a hydrogen pressure of 0.4 MPa. The reaction mixture was subjected to GLC and HPLC analysis to measure conversion, optical purity, and absolute configuration. The results obtained are shown in Table 1.

<GLC analytical conditions> Conversion was measured using a capillary column HP-1 (manufactured by Hewlett Packard).

<HPLC analytical conditions> Optical purity was measured using CHIRALCEL OD (4.6×250 mm, manufactured by Daicel Chemical Industries, Ltd.).

TABLE 1

Asymmetric hydrogenation of N-benzoyl-1-phenylpropenamine

| Reaction Example | L | Conversion (%) | Enantio-selectivity (% ee) | Absolute configuration |
|---|---|---|---|---|
| Example 5 | (S,S)-Me-UCAP-DTBM | 100.0 | 98.7 | S |
| Example 6 | (S,S)-Me-UCAP-DM | 100.0 | 95.4 | S |
| Comparative Example 1 | (R)-BINAP | 6.6 | 34.6 | S |
| Comparative Example 2 | (R,R)-Me-DuPHOS | 25.4 | 77.6 | R |

While the invention has been described in detail and with reference to specific embodiments thereof, it will be apparent to one skilled in the art that various changes and modifications can be made therein without departing from the scope thereof.

This application is based on Japanese patent application No. 2001-375256 filed Dec. 10, 2001, the entire contents thereof being hereby incorporated by reference.

What is claimed is:

1. A phosphine-phospholane compound represented by the formula (1):

wherein $R^1$ represents hydrogen atom, a linear or branched alkyl group having 1 to 4 carbon atoms; $R^2$ represents hydrogen atom or $OR^{21}$, where $R^{21}$ represents an alkyl group having 1 to 4 carbon atoms, a represents an integer of 1 to 2, b represents an integer of 1 to 3, the sum of a and b is 2 or 3, provided that at least one of $R^1$ and $R^2$ is not a hydrogen atom; $R^3$, $R^4$, $R^5$ and $R^6$ are the same or different, and each represents hydrogen atom, an alkyl group having 1 to 6 carbon atoms, or an alkoxy group having 1 to 6 carbon atoms, and each of (1) $R^3$ and $R^4$, (2) $R^4$ and $R^5$, and (3) $R^5$ and $R^6$ may be combined to form a ring which may contain one or more oxygen atoms; and $R^7$ and $R^8$ are the same or different, and each represents (1) a linear or branched alkyl group having 1 to 6 carbon atoms, (2) a cycloalkyl group having 3 to 7 carbon atoms, (3) a perfluoroalkyl group, (4) a phenyl group, (5) a phenyl group having one or more substituents each selected from the group consisting of an alkyl group having 1 to 6 carbon atoms, an alkyl group having 1 to 6 carbon atoms which is substituted by one or more halogen atoms, an alkoxy group having 1 to 6 carbon atoms, and a halogen atom, (6) an aralkyl group having 7 to 12 carbon atoms, or (7) a ring-substituted aralkyl group.

2. A tertiary phosphine-primary phosphine compound represented by the formula (2):

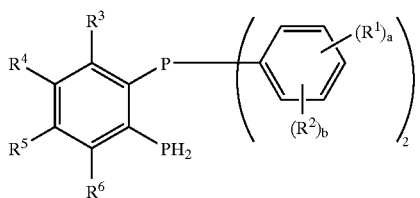

(2)

wherein $R^1$ represents hydrogen atom, a linear or branched alkyl group having 1 to 4 carbon atoms; $R^2$ represents hydrogen atom or $OR^{21}$, where $R^{21}$ represents an alkyl group having 1 to 4 carbon atoms, a represents an integer of 1 to 2, b represents an integer of 1 to 3, the sum of a and b is 2 or 3, provided that at least one of $R^1$ and $R^2$ is not a hydrogen atom; $R^3$, $R^4$, $R^5$ and $R^6$ are the same or different, and each represents hydrogen atom, an alkyl group having 1 to 6 carbon atoms, or an alkoxy group having 1 to 6 carbon atoms, and each of (1) $R^3$ and $R^4$, (2) $R^4$ and $R^5$, and (3) $R^5$ and $R^6$ may be combined to form a ring which may contain one or more oxygen atoms.

3. A transition metal complex comprising the phosphine-phospholane compound represented by the formula (1) of claim 1 and a transition metal, wherein the transition metal is selected from the group consisting of Ir, Rh, Ru, Pd, and Ni.

4. A catalyst for asymmetric syntheses, which comprises the transition metal complex according to claim 3.

5. The catalyst for asymmetric synthetic reactions according to claim 4, wherein the transition metal complex is represented by the formula (3):

$$M_mL_nX_pY_q \quad (3)$$

wherein M is a transition metal selected from the group consisting of Ir, Rh, Ru, Pd, and Ni and L represents the phosphine-phospholane compound represented by the general formula (1) of claim 1; and when M is Ir or Rh, X is Cl, Br, or I, and m=n=p=2 and q=0;

when M is Ru, (i) X is Cl, Br, or I, Y represents a trialkylamino group, and m=n=2, p=4 and q=1, (ii) X is Cl, Br, or I, Y represents pyridyl group or a ring-substituted pyridyl group, and m=n=1, p=2, and q=2, (iii) X is a carboxylate group, and m=n=1, p=2 and q=0, or (iv) X is Cl, Br, or I, and m=n=p=2 and q=0;

when M is Pd, (i) X is Cl, Br, or I, and m=n=1, p=2, and q=0 or (ii) X is an allyl group, and m=n=p=2 and q=0; and when M is Ni, X is Cl, Br, or I, and m=n=1, p=2, and q=0.

6. The catalyst for asymmetric synthetic reaction according to claim 4, wherein the transition metal complex is represented by the formula (4):

$$[M_mL_nX_pY_q]Z_s \quad (4)$$

wherein M is a transition metal selected from the group consisting of Ir, Rh, Ru, Pd, and Ni and L represents the phosphine-phospholane compound represented by the general formula (1) of claim 1; and when M is Ir or Rh, (i) X is 1,5-cyclooctadiene or norbornadiene, Z is $BF_4$, $ClO_4$, OTf, $PF_6$, $SbF_6$, or $BPh_4$, and m=n=p=s=1 and q=0 or (ii) Z is $BF_4$, $ClO_4$, OTf, $PF_6$, $SbF_6$, or $BPh_4$, and m=s=1, n=2 and q=0;

when M is Ru, (i) X is Cl, Br, or I, Y represents an aromatic compound or olefin compound which is a neutral ligand, Z is Cl, Br, I, $I_3$, or a sulfonate, and m=n=p=s=q=1 or (ii) Z is $BF_4$, $ClO_4$, OTf, $PF_6$, $SbF_6$, or $BPh_4$, and m=n=1, p=q=0, and s=2 or (iii) X is Cl, Br, or I, Z is $Me_2NH_2$ or $Et_2NH_2$, and m=n=2, p=5, q=0, s=1; and when M is Pd or Ni, Z is $BF_4$, $ClO_4$, OTf, $PF_6$, $SbF_6$, or $BPh_4$, and m=n=1, p=q=0, and s=2, where Ph represents a phenyl group and Tf represents a triflate group ($SO_2CF_3$).

7. A catalyst for asymmetric hydrogenation, which comprises the transition metal complex according to claim 3.

8. The catalyst according to claim 4, wherein the catalyst is a catalyst for an asymmetric hydrogenation.

* * * * *